US006479463B1

(12) United States Patent
Wang et al.

(10) Patent No.: US 6,479,463 B1
(45) Date of Patent: Nov. 12, 2002

(54) PURINE L-NUCLEOSIDES, ANALOGS AND USES THEREOF

(75) Inventors: Guangyi Wang, Irvine, CA (US); Robert Tam, Irvine, CA (US); Devron Averett, Irvine, CA (US)

(73) Assignee: ICN Pharmaceuticals, Inc., Costa Mesa, CA (US)

( * ) Notice: Subject to any disclaimer, the term of this patent is extended or adjusted under 35 U.S.C. 154(b) by 17 days.

(21) Appl. No.: 09/595,364

(22) Filed: Jun. 16, 2000

Related U.S. Application Data

(62) Division of application No. 09/291,907, filed on Apr. 14, 1999.
(60) Provisional application No. 60/028,586, filed on Oct. 15, 1996, provisional application No. 60/043,974, filed on Apr. 23, 1997, and provisional application No. 60/055,487, filed on Aug. 12, 1997.

(51) Int. Cl.$^7$ .............................................. A61K 31/70
(52) U.S. Cl. ........................... 514/43; 514/45; 514/46; 514/47; 514/48; 536/26.23; 536/26.26; 536/26.7; 536/27.13; 536/27.14; 536/27.6; 536/27.8; 536/27.81
(58) Field of Search .............................. 514/43, 45–48; 536/26.23, 26.26, 26.7, 27.13, 27.14, 27.6, 27.8, 27.81

(56) References Cited

U.S. PATENT DOCUMENTS

| 5,248,776 | A | * | 9/1993 | Chu et al. ..................... 544/310 |
| 5,473,063 | A | * | 12/1995 | Classon et al. ............. 536/122 |
| 5,559,101 | A | * | 9/1996 | Weis et al. ..................... 514/45 |
| 5,561,120 | A | * | 10/1996 | Lin et al. ....................... 514/49 |
| 5,565,438 | A | * | 10/1996 | Chu et al. ..................... 514/50 |
| 5,567,688 | A | * | 10/1996 | Chu et al. ..................... 514/46 |
| 5,567,689 | A | * | 10/1996 | Sommadossi et al. ........ 514/46 |
| 5,587,362 | A | * | 12/1996 | Chu et al. ..................... 514/46 |
| 5,599,796 | A | * | 2/1997 | Schinazi et al. .............. 514/44 |
| 5,627,160 | A | * | 5/1997 | Lin et al. ....................... 514/49 |
| 5,631,239 | A | * | 5/1997 | Lin et al. ....................... 514/49 |

FOREIGN PATENT DOCUMENTS

| EP | 0343945 | * | 11/1989 |
| WO | 8905649 | * | 6/1989 |
| WO | 8905817 | * | 6/1989 |

OTHER PUBLICATIONS

Wong et al., "Photochemical Synthesis of 8–Hydroxyguanine Nucleosides," *Methods in Enzymology*, 234, 59–65 (1994), Month of publication data could not be determined from the copy in hand. Issue Number information is provided whenever possible following the volume number in parentheses. Copy supplied by applicant.*

Goodman, M.G., "Role of Salvage and Phosphorylation int he Immunostimulatory Activity of C8–Substituted Guanine Ribonucleosides," *Journal of Immunology*, 141(7), 2394–2399 (Oct. 1, 1988), Copy supplied by applicant.*

Smee et al., "Broad–Spectrum Activity of 8–Chloro–7–deazaguanosine Against RNA Virus Infections in Mice and Rats," *Antiviral Research*, 26(2), 203–209 (Mar., 1995), Copy supplied by applicant.*

Seela et al., "Alternating d(G–C)$_3$ and d(C–G)$_3$ Hexanucleotides Containing 7–Deaza–2'–deoxyguanosine or 8–Aza–7–deaza–2'deoxyguanosine in Place of dG," *Nucleic Acids Research*, 17(3), 901–910 (Feb. 11, 1989), Copy supplied by applicant.*

Reitz et al., Small–Molecule Immunostimulants. Synthesis and Activity of 7,8–Disubstituted Guanosines and Structurally Related Compounds, *Journal of Medicinal Chemistry*, 37(21), 3561–3578 (Oct. 14, 1994), Copy supplied by applicant.*

Revankar et al., "Thiazolo[4,5–d]pyrimidines. Part II. Synthesis and Anti–human Cytomegalovirus Activity in vitro of certain Acyclonucleosides and Acyclonucleotides Derive3d from the Guanine Analgoues 5–Aminothiazolo[4,5–d]pyrimidine–2,7(3H,6H)–dione," *Antiviral Chemistry & Chemotherapy*, 9(1), 53–63 (Jan., 1998), Copy supplied by applicant.*

Rida et al., "Synthesis of Novel Thiazolo[4,5–d]pyrimidine Derivatives for Antimicrobial, Anti–HIV, and Anticancer Investigation," *Pharmazie*, 51(12), 927–931 (1996), Month of publication data could not be determined from the copy in hand. Issue Number information is provided whenever possible following the volume number in parentheses. Copy supplied by applicant.*

H. Vorbrüggen & C. Ruh–Pohlenz, *Handbook of Nucleoside Synthesis*, John Wiley & Sons, Inc., New York, NY, 2001, ISBN 0–471–09383–1, Month of publication data could not be determined from the copy in hand. Issue Number information is provided whenever possible following the volume number in parentheses.*

* cited by examiner

*Primary Examiner*—Johann Richter
*Assistant Examiner*—L. Eric Crane
(74) *Attorney, Agent, or Firm*—Rutan & Tucker, LLP; Robert D. Fish

(57) ABSTRACT

Novel purine L-nucleoside compounds are disclosed, in which both the purine rings and the sugar are either modified, functionalized or both. The novel compounds or pharmaceutically acceptable esters or salts thereof may be used in pharmaceutical compositions, and such compositions may be used to treat an infection, an infestation, a neoplasm, or an autoimmune disease. The novel compounds may also be used to modulate aspects of the immune system, including modulation of Th1 and Th2.

5 Claims, 7 Drawing Sheets

PURINE L-NUCLEOSIDES, ANALOGS AND USES THEREOF

This is a division of U.S. application Ser. No. 09/291,907, filed Apr. 14, 1999, which claims priority to provisional application Ser. No. 60/028,586, filed Oct. 15, 1996, provisional application Ser. No. 60/043,974, filed Apr. 23, 1997, and provisional application Ser. No. 60/055,487, filed Aug. 12, 1997.

FIELD OF THE INVENTION

The present invention relates to the field of L-nucleosides.

BACKGROUND OF THE INVENTION

The last few decades have seen significant efforts expended in exploring possible uses of D-nucleoside analogs as antiviral agents. Some of this work has borne fruit, and a number of nucleoside analogs are currently being marketed as antiviral drugs, including the HIV reverse transcriptase inhibitors (AZT, ddI, ddC, d4T, and 3TC).

A variety of purine D-nucleoside analogs have also been explored in search of immuno-modulators. Guanosine analogs having substituents at the 7- and/or 8-positions, for example, have been shown to stimulate the immune system (for a review, see: Weigle, W. O. CRC *Crit. Rev. Immunol.* 1987, 7, 285; Lin et al. *J. Med. Chem.* 1985, 28, 1194–1198; Reitz, et al. *J Med. Chem.* 1994, 37, 3561–3578, Michael et al. *J Med. Chem.* 1993, 36, 3431–3436). Certain 3-∃-D-ribofuranosylthiazolo[4,5-d]pyrimidines have also demonstrated significant immunoactivity, including murine spleen cell proliferation and in vivo activity against Semliki Forest virus (Nagahara, et al. *J. Med. Chem.* 1990, 33, 407–415; Robins et al. U.S. Pat. No. 5,041,426). In other research, 7-Deazaguanosine and analogs have been shown to exhibit antiviral activity in mice against a variety of RNA viruses, even though the compound lacks antiviral properties in cell culture. 3-Deazaguanine nucleosides and nucleotides have also demonstrated significant broad spectrum antiviral activity against certain DNA and RNA viruses (Revankar et al. *J. Med. Chem.* 1984, 27, 1389–1396). Certain 7- and 9-deazaguanine C-nucleosides exhibit the ability to protect mice against a lethal challenge of Semliki Forest virus (Girgis et al. *J. Med. Chem.* 1990, 33, 2750–2755). Certain 6-sulfenamide and 6-sulfinamide purine nucleosides have demonstrated significant antitumor activity (Robins et al. U.S. Pat. No. 4,328,336). Certain pyrimido[5,4-D] pyrimidine nucleosides were effective in treatment against L1210 in BDF1 mice (Robins et al. U.S. Pat. No. 5,041,542), and there, the antiviral and antitumor activities of the above mentioned nucleosides were suggested to be the results of the their role as immunomdulators (Bonnet et al. *J med. Chem.* 1993, 36, 635–653).

One possible target of immunomodulation involves stimulation or suppression of Th1 and Th2 lymphokines. Type I (Th1) cells produce interleukin 2 (IL-2), tumor necrosis factor (TNF∀) and interferon gamma (IFN( ) and they are responsible primarily for cell-mediated immunity such as delayed type hypersensitivity and antiviral immunity. Type 2 (Th2) cells produce interleukins, IL4, IL-5, IL-6, IL-9, IL-10 and IL-13 and are primarily involved in assisting humoral immune responses such as those seen in response to allergens, e.g. IgE and IgG4 antibody isotype switching (Mosmann, 1989, *Annu Rev Immunol*, 7:145–173). D-guanosine analogs have been shown to elicit various effects on lymphokines IL-1, IL-6, IFN∀ and TNF∀ (indirectly) in vitro (Goodman, 1988, *Int J Immunopharmacol*, 10, 579–88) and in vivo (Smee et al., 1991, *Antiviral Res* 15: 229). However, the ability of the D-guanosine analogs such as 7- thio-8-oxoguanosine to modulate Type I or Type 2 cytokines directly in T cells was ineffective or had not been described.

Thus, there remains a need for novel L-nucleoside analogs, including novel purine L-nucleoside analogs. There is a particular need for novel purine L-nucleosides which have immunomodulatory activity, and especially for novel purine L-nucleosides which modulate Th1 and Th2 activity.

BRIEF DESCRIPTION OF THE INVENTION

The present invention is directed to novel purine L-nucleoside compounds, their therapeutic uses and synthesis.

In one aspect of the invention, there are provided purine L-nucleoside, analogs of Formula I.

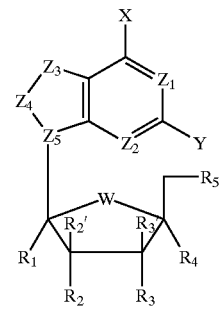

Formula I wherein $R_1$, $R_2$, $R_3$, $R_4$, $R_5$, $R_2'$ and $R_3'$ are independently selected from the group consisting of
H, OH, $NH_2$, F, Cl, Br, I, $N_3$, —CN, —OR', —NR'$_2$, —SR', —$NHNH_2$, —NHOH, CHO, COOR', CONR'$_2$, alkyl, alkenyl, alkylnyl, aryl, aralkyl, substituted alkyl, substituted alkenyl, substituted alkynyl, substituted aryl, substituted aralkyl, where the substituent is selected from F, Cl, Br, I, $N_3$, —CN, —OR", $NO_2$, —NR"$_2$, SR", —$NHNH_2$, —NHOH, COOR", CONR"$_2$ and where R' and R" are H, alkyl, alkenyl, alkynyl, aryl, aralkyl;

W=O, S, $CH_2$, Se;

$Z_1$, $Z_2$ are independently selected from N, C, CH;

$Z_3$, $Z_4$, $Z_5$, are independently selected from the group consisting of —CR—, —NR—, —O—, —S—, —Se—, —C=O, —C=S, —S=O, —CR=CR—, —CR=N—, —N=N—, where R is selected from the group consisting of H, F, Cl, Br, I, $N_3$, —CN, —OR', —NR'$_2$, —SR', —$NHNH_2$, —NHOH, —$NO_2$, CHO, COOR', $CONH_2$, —C(O)—$NH_2$, —C(S)—$NH_2$, —C(NH)—$NH_2$, —C(NOH)—$NH_2$, =O, =NH, =NOH, =NR, alkyl, alkenyl, aralkyl, aryl, aralkyl, substituted alkyl, substituted alkenyl, substituted alkynyl, substituted aryl, substituted aralkyl, where the substituent is selected from H, —OH, $NH_2$, F, Cl, Br, I, $N_3$, —CN, —COOR", —CONR"$_2$, —OR", —NR"$_2$, —SR", —$NHNH_2$, —NHOH, —$NO_2$, and R', R" are H, alkyl, alkenyl, alkynyl, aryl, aralkyl, acetyl, acyl, sulfonyl;

The Chemical bond between $Z_3$ and $Z_4$ or $Z_4$, and $Z_5$ is selected from C—C, C=C, C—N, C=N, N—N, N=N, C—S, N—S;

X and Y are independently selected from the group consisting of H, OH, $NH_2$, F, Cl, Br, I, $N_3$, —S—$NH_2$, —S(O)—$NH_2$, —S($O_2$)—$NH_2$, —CN, —COOR', —CONR'$_2$, —OR', —NR'$_2$, —SR', —NHN$H_2$, —NHOH, alkyl, alkenyl, alkylnyl, aryl, aralkyl, substituted alkyl, substituted alkenyl, substituted alkynyl, substituted aryl, substituted aralkyl, where the substituent is selected from F, Cl, Br, I, $N_3$, —CN, —OR", $NO_2$, —NR"$_2$, SR", —NHN$H_2$, —NHOH, and R', R" are H, alkyl, alkenyl, alkynyl, aryl, aralkyl;

with the proviso that where W is O, and where $R_1$ and $R_4$ are H, and where $R_2$, $R_3$, and $R_5$ are OH, then $Z_1$, $Z_2$, and $Z_5$ are not N, $Z_3$ is not S, $Z_4$ is not CO, Y is not $NH_2$, and X is not OH;

In another aspect of the invention, a pharmnaceutical composition comprises a therapeutically effective amount of a compound of Formula I, or a pharmaceutically acceptable ester or salt thereof admixed with at least one pharnacutically acceptable carrier.

In yet another aspect of the invention a compound according to Formulas I is used in the treatment of any condition which responds positively to administration of the compound, and according to any formulation and protocol which achieves the positive response. Among other things it is contemplated that compounds of Formula I may be used to treat an infection, an infestation, a cancer, tumor or other neoplasm, or an autoimmune disease.

DETAILED DESCRIPTION

Figure 1:
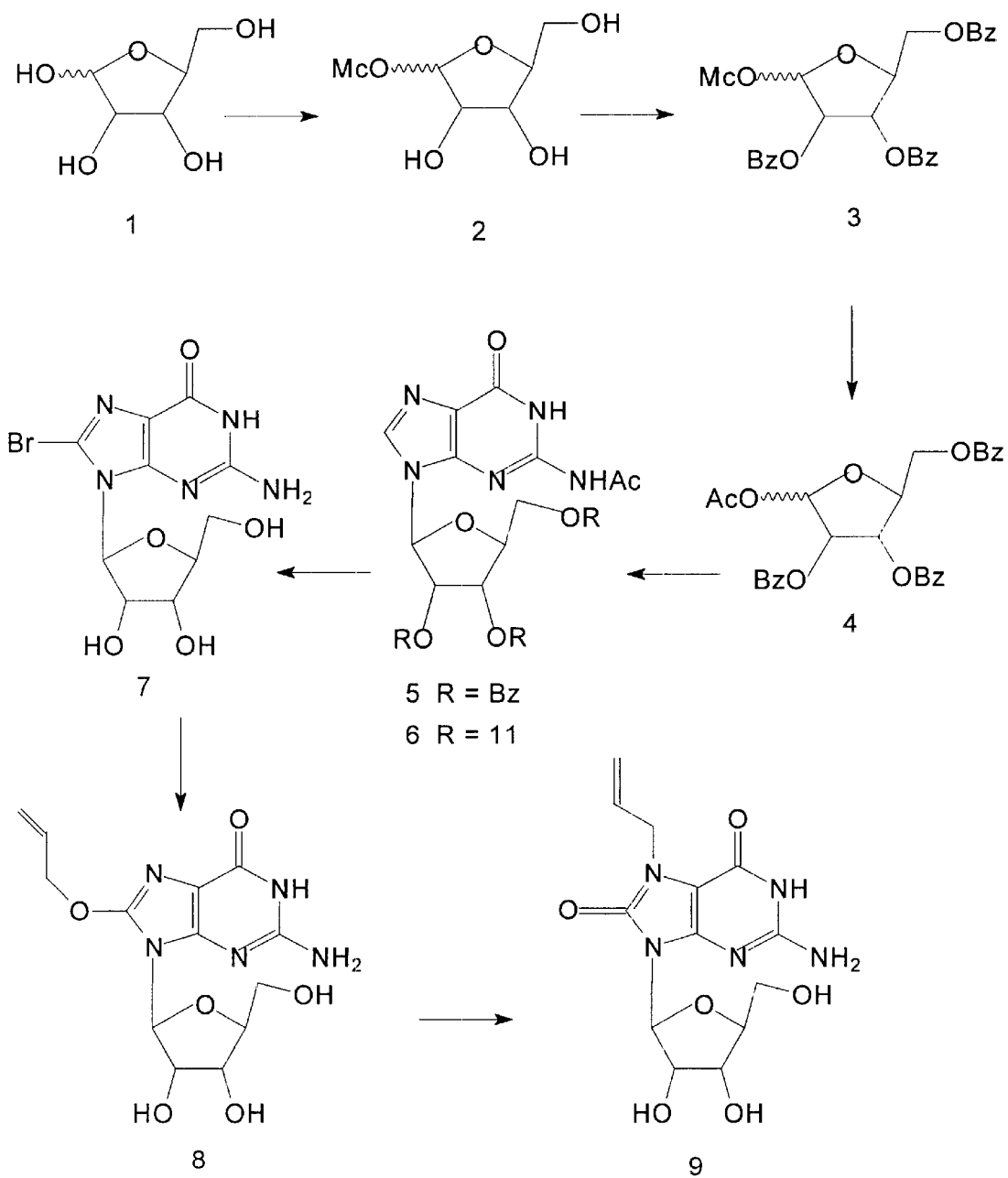
FIGS. 1–6 (Schemes 1–6) depict synthetic chemical steps which may be used to synthesize the compounds according to the present invention. Schemes pertaining to the synthesis of a particular composition are referenced in the examples set forth herein.
Figure 2:
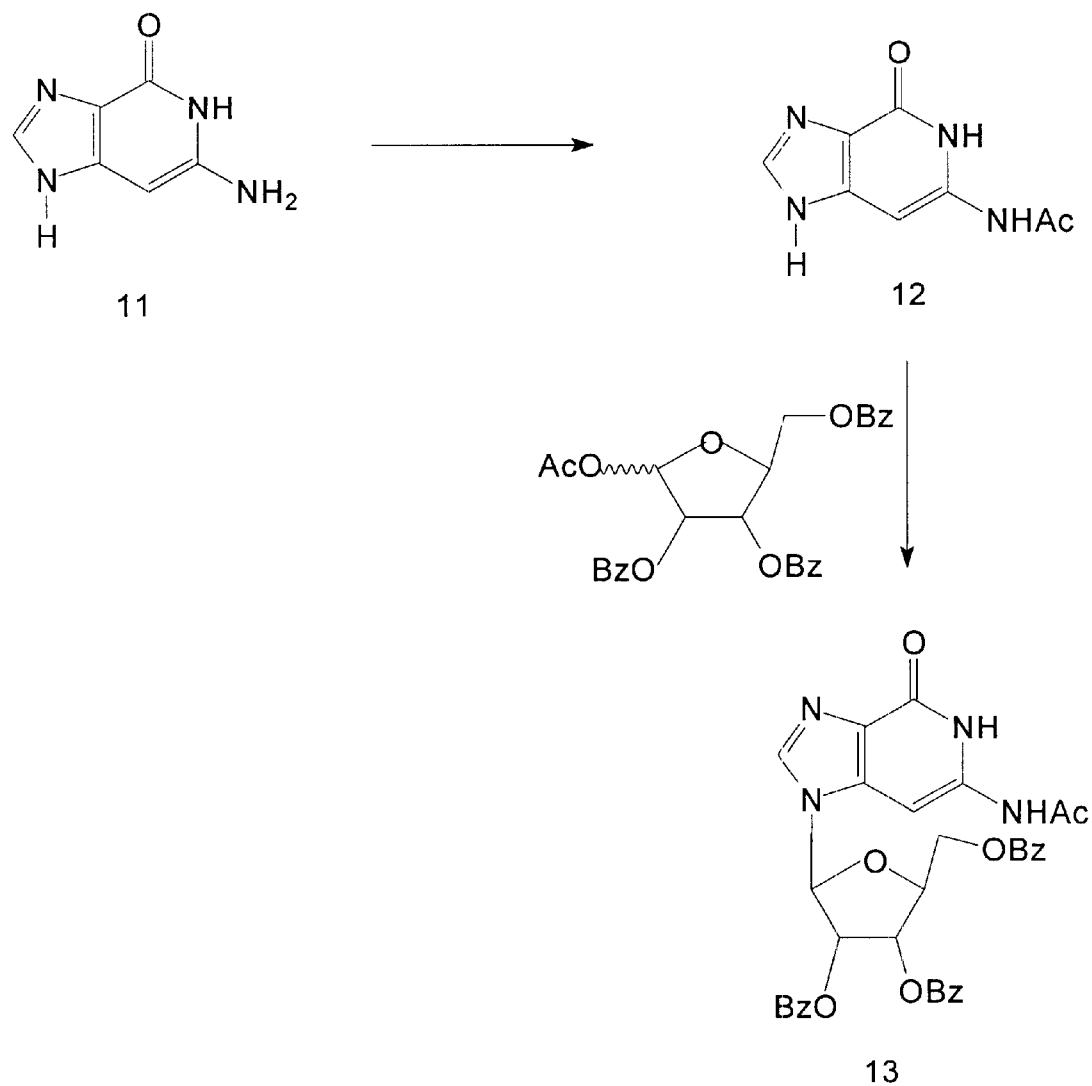
Figure 3:
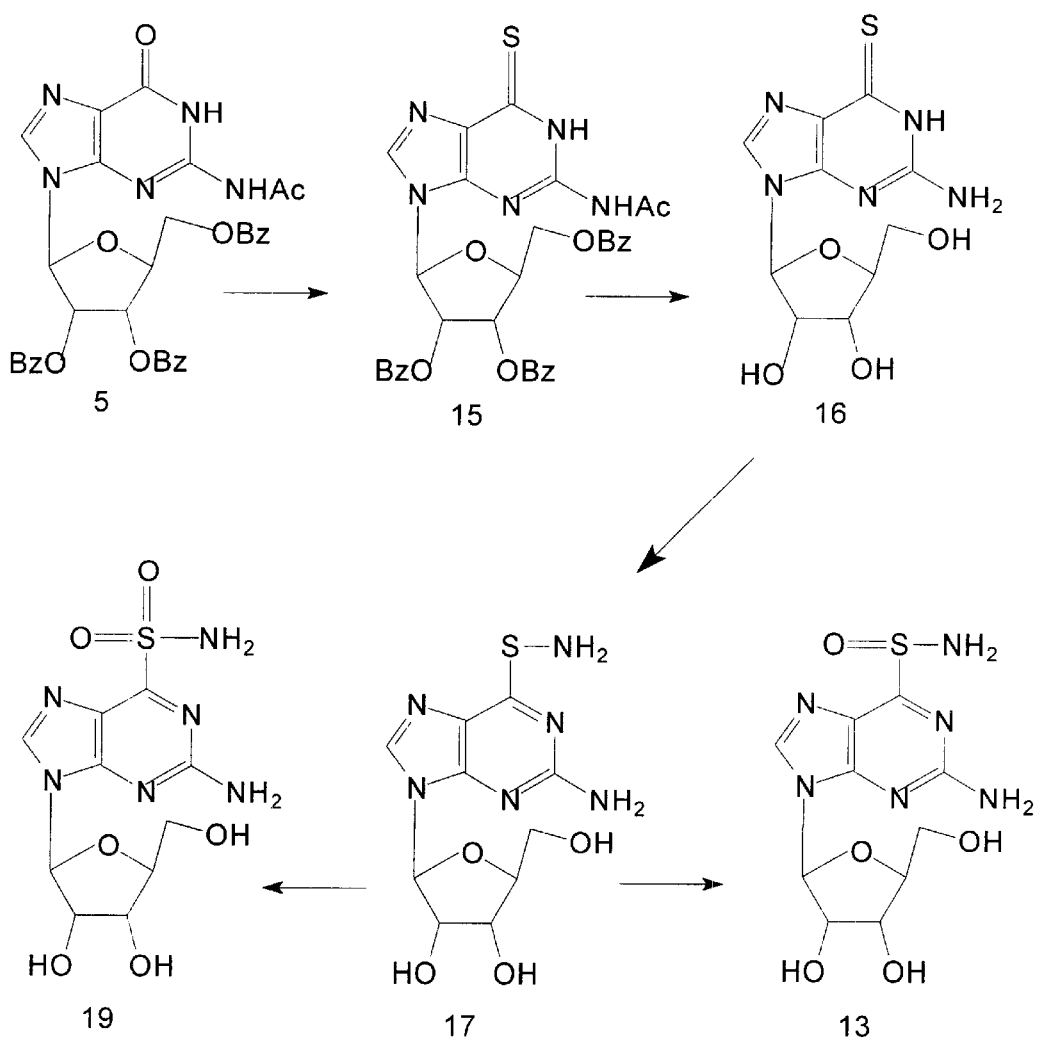
Figure 4:
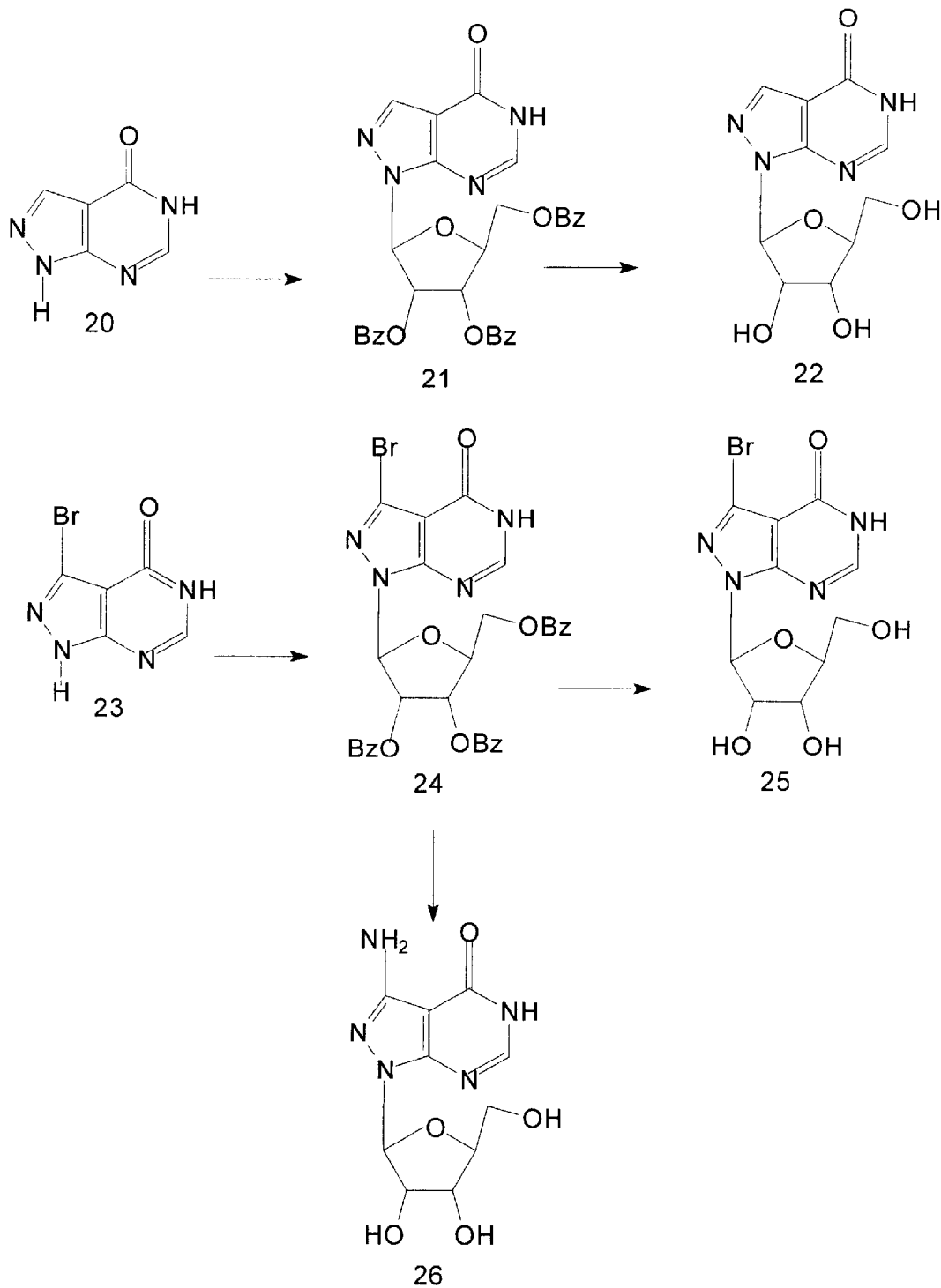
Figure 5:
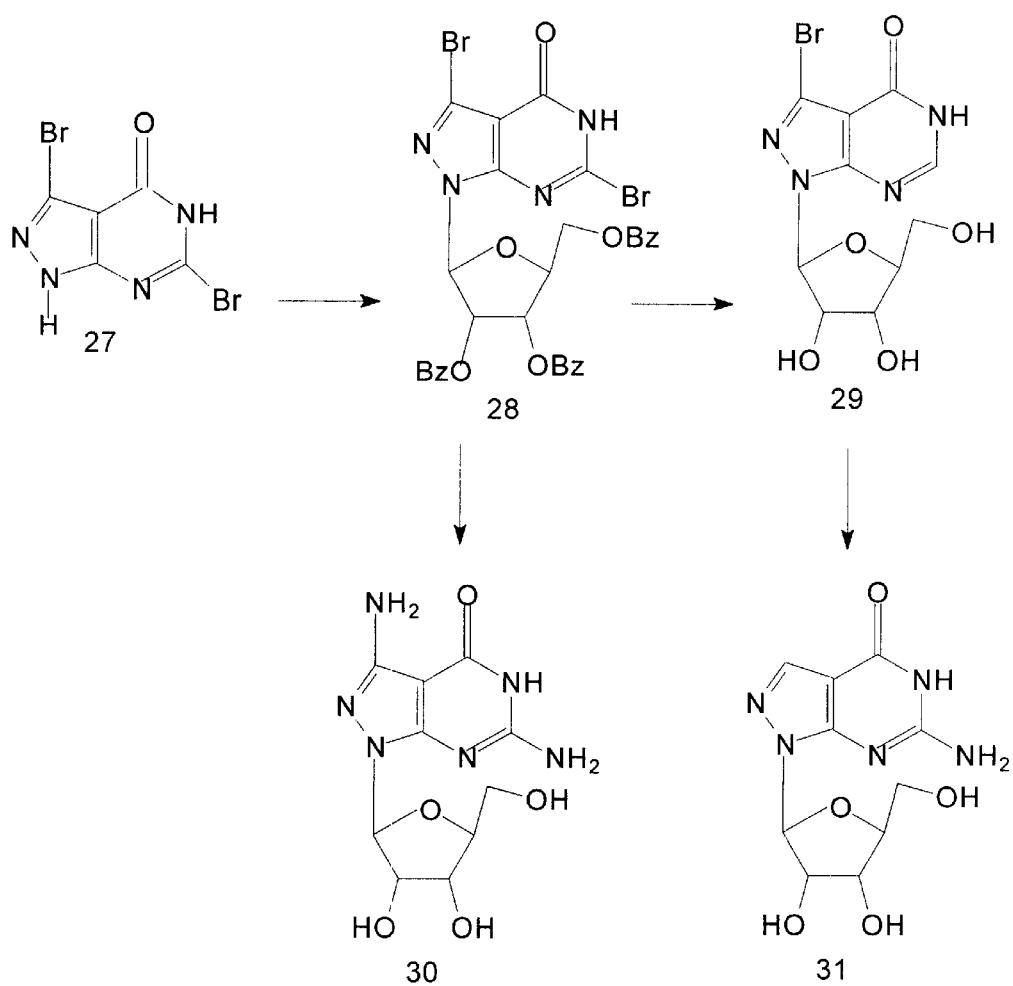
Figure 6:
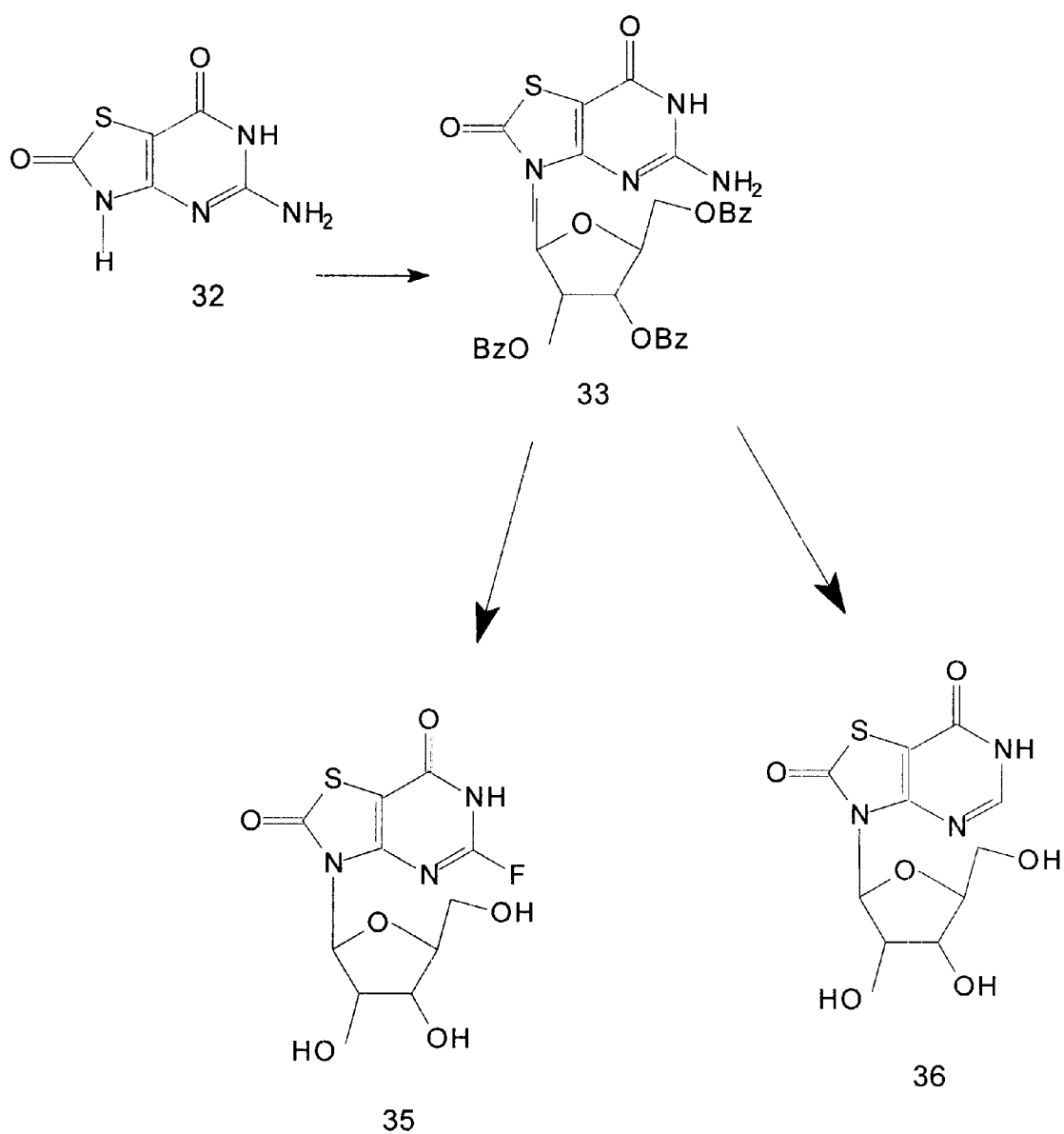

Where the following terms are. used in this specification, they are. used as defined below.

The term "nucleoside" refers to a compound composed of any pentose or modified pentose moiety attached to a specific position of a heterocycle or to the natural position of a punne (9-position) or pyrimidine (1-position) or to the equivalent position in an analog.

The term "nucleotide" refers to a phosphate ester substituted on the 5'-position of a nucleoside.

The term "heterocycle" refers to a monovalent saturated or unsaturated carbocyclic radical having at least one hetero atom, such as N, O or S, within the ring each available position of which can be optionally substituted, independently, with, e.g., hydroxy, oxo, amino, imino, lower alkyl, bromo, chloro and/or cyano. Included within this class of substituents are purines, pyrimidines.

The term "purine" refers to nitrogenous bicyclic heterocycles.

The term "pyrimidine" refers to nitrogenous monocyclic heterocycles.

The term "D-nucleosides" that is used in the present invention describes the nucleoside compounds that have a D-ribose sugar moiety (e.g., Adenosine).

The term "L-nucleosides" that is used in the present invention describes the nucleoside compounds that have an L-ribose sugar moiety.

The term "L-configuration" is used throughout the present invention to describe the chemical configuration of the ribofuranosyl moiety of the compounds that is linked to the nucleobases. The L-configuration of the sugar moiety of compounds of the present invention contrasts with the D-configuration of ribose sugar moieties of the naturally occurring nucleosides such as cytidine, adenosine, thymidine, guanosine and uridine.

The term "C-nucleosides" is used throughout the specification to describe the linikage type that formed between the ribose sugar moiety and the heterocyclic base. In C-nucleosides, the linkage originates from the C-1 position of the ribose sugar moiety and joins the carbon of the heterocyclic base. The linkage that forms in C-nucleosides are carbon to carbon type.

The term "N-nucleosides" is used throughout the specification to describe the linkage type that formed between the ribose sugar moiety and the heterocyclic base. In N-nucleosides, the linkage originates from the C-1 position of the ribose sugar moiety and joins the nitrogen of the heterocyclic base. The linkage that forms in N-nucleosides are carbon to nitrogen type.

The term "protecting group" refers to a chemical group that is added to oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term "lower alkyl" refers to methyl, ethyl, n-propyl, isopropyl, n-butyl, t-butyl, i-butyl or n-hexyl. This term is further exemplified to a cyclic, branched or straight chain from one to six carbon atoms.

The term "aryl" refers to a monovalent unsaturated aromatic carbocyclic radical having a single ring (e.g., phenyl) or two condensed rings (e.g., naphthyl), which can optionally be substituted with hydroxyl, lower alky, chloro, and/or cyano.

The term "heterocycle" refers to a monovalent saturated or unsaturated carbocyclic radical having at least one hetero atom, such as N, O, S, Se or P, within the ring, each available position of which can be optionally substituted or unsubstituted, independently, with hydroxy, oxo, amino, imino, lower alkyl, bromo, chloro, and/or cyano.

The term "monocyclic" refers to a monovalent saturated carbocyclic radical having at least one hetero atom, such as O, N, S, Se or P, within the ring, each available position of which can be optionally substituted, independently, with a sugar moiety or any other groups like bromo, chloro and/or cyano, so that the monocyclic ring system eventually aromatized [e.g., Thymidine; 1-(2'-deoxy-ᴣ-D-erythro-pentofuranosyl)thymine].

The term "immunomodulators" refers to natural or synthetic products capable of modifying the normal or aberrant immune system through stimulation or suppression.

The term "effective amount" refers to the amount of a compound of formula (I) which will restore immune function to normal levels, or increase immune function above normal levels in order to eliminate infection.

The compounds of Formulas I and I-A through I-F may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the compounds of Formula I.

The term "α" and "β" indicate the specific stereochemical configuration of a substituent at an asymmetric carbon atom in a chemical structure as drawn. The compounds described herein are all in the L-furanosyl configuration.

The term "enantiomers" refers to a pair of stereoisomers that are non-superimposable mirror images of each other. A mixture of a pair of enantiomers, in a 1:1 ratio, is a "racemic" mixture.

The term "isomers" refers to different compounds that have the same formula. "Stereoisomers" are isomers that differ only in the way the atoms are arranged in space.

"Pharmaceutically acceptable salts" may be any salts derived from inorganic and organic acids or bases.

Compounds

The compounds of the present invention are generally described by Formula I. There are, however, several subsets of compounds which are of particular interest, including compounds according to Formulas I-A through I-F below.

Formula I-A compounds are 8-substituted α- or β-L-guanosine analogs having the structure:

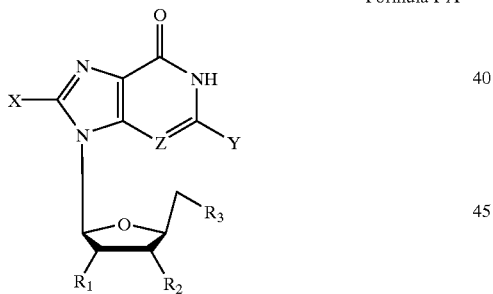

Formula I-A wherein X is selected from H, R, F, Cl, Br, I, $N_3$, —CN, —OR, —SR, —$NR_2$, —$NHNH_2$, —NHOH, —CHO, —$CONH_2$, —COOR, and -L-A; where R is selected from alkyl, alkenyl, alkynyl, and aralkyl, acetyl, acyl, sulfonyl; L is a linker and selected from alkyl, alkenyl, alkynyl, and aralkyl; and A is selected from H, —OR', —SR', —$NR'_2$, —$NHNH'_2$, —CHO, —COOR', —$CONR'_2$, where R' is selected from H, Me, Et, allyl, acetyl, —$COCF_3$;

Y is selected from H, R, F, Cl, Br, I, $N_3$, CN, OR, SR, $NR_2$, where R is selected from H, alkyl, alkenyl, alkynyl and aralkyl, acetyl, acyl, sulfonyl;

Z is N or CH; and $R_1$, $R_2$, and $R_3$ are independently selected from H, —OH, —OAc, —OBz, —OP($O_2$)OH;

with the proviso that where $R_1$, $R_2$, and $R_3$ are OH, then Z is not N, Y is not $NH_2$, and X is not H, and with the proviso that where $R_1$, $R_2$, and $R_3$ are OH, then Z is not CH, Y is not NH((CO)$CH_3$), and X is not H.

Formula IB compounds are 7-substituted-8-oxo-α- or β-L-guanosine analogs having structure:

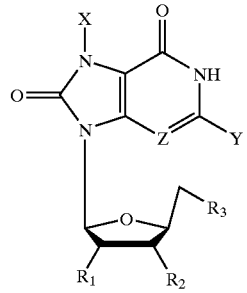

Formula I-B wherein X is selected from H, R, —$NH_2$, —CHO, —COOR, -L-A, where R is selected from alkyl, alkenyl, alkynyl, and aralkyl; L is a linker and selected from alkyl, alkenyl, alkynyl, and aralkyl; A is selected from H, F, Cl, Br, I, —OR', —SR', —$NR'_2$, —$NHNH_2$, —NHOH, $N_3$, —CHO, —$CONH_2$, —COOR', —CN, where R' is selected from Me, Et, allyl, acetyl, —$COCF_3$;

Y is selected from H, R, F, Cl, Br, I, $N_3$, —CN, —OR, —SR, —$NR_2$, where R is selected from H, alkyl, alkenyl, alkynyl, and aralkyl, acetyl, acyl, sulfonyl;

Z is N or CH;

$R_1$, $R_2$, and $R_3$ are independently selected from H, —OH, —OAc, —OBz, —OP($O_2$)OH;

with the proviso that where $R_1$, $R_2$, and $R_3$ are OH, then Z is not N, and Y is not $NH_2$, and X is not propyl.

Formula I-C compounds are 7-deaza-7,8-mono- or disubstituted α- or β-L-guanosine analogs having the structure:

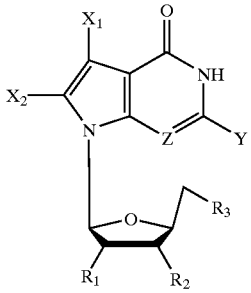

Formula I-C wherein $X_1$ and $X_2$ are independently selected from H, R, F, Cl, Br, I, $N_3$, —CN, —OR, —SR, —$NR_2$, —$NHNH_2$, —NHOH, —CHO, $CONH_2$, —COOR, and -L-A, where R is selected from alkyl, alkenyl, alkynyl, and aralkyl, acetyl, acyl, sulfonyl; L is a linker and selected from alkyl, alkenyl, alkynyl, and aralkyl; and A is selected from H, —OR', —SR', —$NR'_2$, —$NHNH'_2$, —CHO, —COOR', —$CONR'_2$, where R' is selected from H, Me, Et, allyl, acetyl, —$COCF_3$;

Y is selected from H, R, ,F Cl, Br, I, $N_3$, —CN, —OR, —SR, —$NR_2$, where R is selected from H, alkyl, alkenyl, alkynyl, and aralkyl acetyl, acyl, sulfonyl;

Z is N or CH;

$R_1$, $R_2$, and $R_3$ are independently selected from H, —OH, —OAc, —OBz, —OP($O_2$)OH;

with the proviso that where $R_1$, $R_2$, and $R_3$ are OH, then Z is not N, Y is not H, and $X_1$ is not carboxamidoxime and $X_2$ is not H.

Formula I-D compounds are 7-deaza-8-aza-7-substituted α- or β-L-guanosine analogs having the structure:

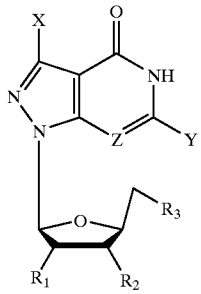

Formula I-D

X is selected from H, R, F, Cl, Br, I, $N_3'$, —CN, —OR, —SR, —$NR_2$, —$NHNH_2$, —NHOH, —CHO, —$CONH_2$, —COOR, and -L-A; where R is selected from alkyl, alkenyl, alkynyl, and aralkyl, acetyl, acyl, sulfonyl; L is a linker and selected from alkyl, alkenyl, alkynyl, and aralkyl; and A is selected from H, —OR', SR', —$NR'_2$, —$NHNH'_2$, —CHO, —COOR', —$CONR'_2$, where R' is selected from H, Me, Et, allyl, acetyl, —$COCF_3$;

Y is selected from H, R, F, Cl, Br, I, $N_3$, —CN, —OR, —SR, —NR2, where R is selected from H, alkyl, alkenyl, alkynyl, and aralkyl, acetyl, acyl, sulfonyl;

Z is N or CH;

$R_1$, $R_2$, and $R_3$ are independently selected from H, —OH, —OAc, —OBz, —OP($O_2$)OH.

Formula I-E compounds are thiazolo[4,5-d]pyrimidine α- or β-L-nucleosides having the structure:

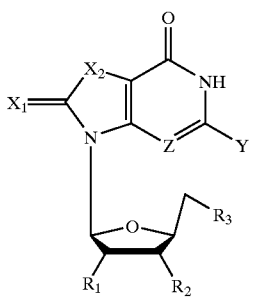

Formula I-E $X_1$=O, S, =NH, =$NHNH_2$, =NHOH, =NR where R is selected from alkyl, alkyenyl, alkynyl, and aralkyl, acyl;

$X_2$ is S, O, or Se

Y is selected from H, R, F, Cl, Br, I, $N_3$, —CN, —OR, —SR, —$NR_2$, where R is selected from H, alkyl, alkenyl, alkynyl, and aralkyl, acetyl, acyl, sulfonyl;

Z is N or CH;

$R_1$, $R_2$, and $R_3$ are independently selected from H, —OH, —OAc, —OBz, —OP($O_2$)OH.

Formula I-F compounds are β-L-purine nucleosides having the structure:

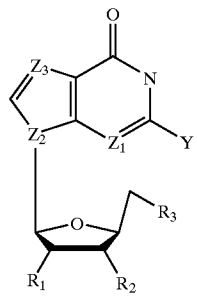

Formula I-F

X is selected from H, R, —$SNH_2$, —$S(O)NH_2$, —$SO_2NH_2$, F, Cl, Br, I, $N_3$, —CN, —OR, —SR, —$NR_2$, where R is selected from H, alkyl, alkenyl, alkynyl, and aralkyl, acetyl, acyl, sulfonyl;

Y is selected from H, R, F, Cl, Br, I, $N_3$, —CN, —OR, —SR, —$NR_2$, where R is selected from H, alkyl, alkenyl, alkynyl, and aralkyl, acetyl, acyl, sulfonyl;

$Z_1$, $Z_2$ and $Z_3$ are independently selected from C, N, and CH;

$R_1$, $R_2$, and $R_3$ are independently selected from H, —OH, —OAc, —OBz, —OP($O_2$)OH.

Uses

It is contemplated that compounds according to Formulas I, II, III, IV and V, the compounds of the present invention, will be used to treat a wide variety of conditions, and in fact any condition which responds positively to administration of one or more of the compounds. Among other things it is specifically contemplated that compounds of the invention may be used to treat an infection, an infestation, a cancer or tumor or an autoimmune disease.

Infections contemplated to be treated with the compounds of the present invention include respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), measles and fungus.

Infestations contemplated to be treated with the compounds of the present invention include protozoan infestations, as well as helminth and other parasitic infestations. Cancers or tumors, contemplated to be treated include those caused by a virus, and the effect may involve inhibiting the transformation of virus-infected cells to a neoplastic state, inhibiting the spread of viruses from transformed cells to other normal cells and/or arresting the growth of virus-transformed cells.

Autoimmune and other diseases contemplated to be treated include arthritis, psoriasis, bowel disease, juvenile diabetes, lupus, multiple sclerosis, gout and gouty arthritis, rheumatoid arthritis, rejection of transplantation, allergy and asthma.

Still other contemplated uses of the compounds according to the present invention include use as intermediates in the chemical synthesis of other nucleoside or nucleotide analogs which are, in turn, useful as therapeutic agents or for other purposes.

In yet another aspect, a method of treating a mammal comprises administering a therapeutically and/or prophylactically effective amount of a pharmaceutical containing a compound of the present invention. In this aspect the effect may relate to modulation of some portion of the mammal's immune system, especially modulation of lymphokines profiles of Th1 and Th2. Where modulation of Th1 and Th2 lymphokines occurs, it is contemplated that the modulation may include stimulation of both Th1 and Th2, suppression of both Th1 and Th2, stimulation of either Th1 or Th2 and suppression of the other, or a bimodal modulation in which one effect on Th1/Th2 levels (such as generalized suppression) occurs at a low concentration, while another effect (such as stimulation of either Th1 or Th2 and suppression of the other) occurs at a higher concentration.

In general, the most preferred uses according to the present invention are those in which the active compounds are relatively less cytotoxic to the non-target host cells and relatively more active against the target. In this respect, it may also be advantageous that L-nucleosides may have increased stability over D-nucleosides, which could lead to better pharmacokinetics. This result may attain because L-nucleosides may not be recognized by enzymes, and therefore may have longer half-lives.

It is contemplated that compounds according to the present invention will be administered in any appropriate pharmaceutical formulation, and under any appropriate. protocol. Thus, administration may take place orally, parenterally (including subcutaneous injections, intravenous, intramuscularly, by intrasternal injection or infusion techniques), by inhalation spray, or rectally, topically and so forth, and in dosage unit formulations containing conventional non-toxic pharmaceutically acceptable carriers, adjuvants and vehicles.

By way of example, it is contemplated that compounds according to the present invention can be formulated in admixture with a phannaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage, of favorable pharmacokinetic parameters of the pro-drug forms, where applicable, in delivering the present compounds to a targeted site within the host organism or patient to maximize the intended effect of the compound.

In addition, compounds according to the present invention may be administered alone or in combination with other agents for the treatment of the above infections or conditions. Combination therapies according to the present invention comprise the administration of at least one compound of the present invention or a functional derivative thereof and at least one other pharmaceutically active ingredient. The active ingredient(s) andpharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect. Preferably the combination therapy involves the administration of one compound of the Present invention or aphysiologically functional derivative thereof and one of the agents mentioned herein below.

Examples of such further therapeutic agents include agents that are effective for the modulation of immune system or associated conditions such as AZT, 3TC, 8-substituted guanosine analogs, 2',3'-dideoxynucleosides, interleukin II, interferons such as α-interferon, tucaresol, levamisole, isoprinosirie and cyclolignans. Certain compounds according to the present invention may be effective for enhancing the biological activity of certain agents according to the present invention by reducing the metabolism or inactivation of other compounds and as such are co-administered for this intended effect.

With respect to dosage, one of ordinary skill in the art will recognize that a therapeutically effective amount will vary with the infection or condition to be treated, its seventy, the treatment regimen to be employed, the phaimacokinetics of the agent used, as well as the patient (animal or human) treated. Effective dosages may range from 1 mg/kg of body weight, or less, to 25 mg/kg of body weight or more. In general a therapeutically effective amount of the present compound in dosage form usually ranges from slightly less than about 1 mg./kg. to about 25 mg./kg. of the patient, depending upon the compound used, the condition or infection treated and the route of administration. This dosage range generally produces effective blood level concentrations of active compound ranging from about 0.04 to about 100 micrograms/cc of blood in the patient. It is contemplated, however, that an appropriate regimen will be developed by administering a small amount, and then increasing, the amount until either the side effects become unduly adverse, or the intended effect is achieved.

Administration of the active compound may range from continuous (intravenous drip) to several oral administrations per day (for example, Q.I.D.) and may include oral, topical, parenteral, intramuscular, intravenous, subcutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably. intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable, carriers and additives including water, glycols, oils, alcohols, flavouring agents, preservatives, colouring agents and the like may be used. For solid oral preparations such as powders, tablets, capsules, and for solid preparations such as suppositories suitable carriers and additives including starches. sugar carrier, such as dextrose, mannitol, lactose and related carriers, diluents, granulating agents, lubricants, binders, disintegrating agents and the like may be used. If desired the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Test Results

In vitro tests were performed on nine L-guanosine compounds and the results are described below. The nine compounds were as follows:

17316 8-mercapto-L-guanosine
17317 2-amino-9-β-L-ribofuranosylpurine-6-sulfenamide
17318 2-amino-9-β-L-ribofuranosylpurine-6-sulfinamide
17319 2-amino-9-β-L-ribofuranosylpurine-6-sulfnamide
17320 7-deaza-8-aza-β-L-guanosine
17321 7-deaza-8-aza-7-amino-β-L-guanosine
17322 7-deaza-8-aza-7-bromo-β-L-guanosine
17324 8-Allyloxy-β-L-guanosine Peripheral blood mononuclear cells (PBMCs) were isolated from the buffy coat following Ficoll-Hypaque density gradient centrifugation of 60 ml blood from healthy donors. T-cells were then purified from the PBMCs using Lymphokwik lymphocyte isolation reagent specific for T-cells (LK-25T, One Lambda, Canoga Park Calif.). An average yield of 40–60×$10^6$ T-cells were then incubated overnight at 37° C. in 20–30 ml RPMI-AP5 (RPMI-1640 medium (ICN, Costa Mesa, Calif.) containing 20 mM HEPES buffer, pH 7.4, 5% autologous plasma, 1% L-glutamine, 1% penicillin/ streptomycin and 0.05% 2-mercaptoethanol) to remove any contaminating adherent cells. In all experiments, T-cells were washed with RPMI-AP5 and then plated on 96-well microtitre plates at a cell concentration of 1×$10^6$ cells/ml.

The T-cells were activated by the addition of 500 ng ionomycin and 10 ng phorbol 12-myristate 13-acetate (PMA) (Calbiochem, La Jolla, Calif.) and incubated for 48–72 h at 37° C. PMA/ionomycin-activated T-cells were treated with 0.5–50 μM of the L-guanosine being tested, or with 250–10000 U/ml of a control antiviral, interferon-alpha (Accurate, Westbury, N.Y.) immediately following activation and re-treated 24 h later. T-cells from each plate were used for immunofluorescence analysis and the supernatants used for extracellular cytokine measurements. Following activation, 900 μl cell supernatant from each microplate was transferred to another microplate for analysis of cell-derived cytokine production. The cells are then used in immunofluorescence analyses for intracellular cytokine levels and cytokine receptor expression.

Cell-derived human cytokine concentrations were determined in cell supernatants from each microplate. Activation-induced changes in interleukin-2 (IL-2) levels were determined using a commercially available ELISA kit (R & D systems Quantikine kit, Minneapolis, Minn.) or by bioassay using the IL-2-dependent cell line, CTLL-2 (ATCC, Rockville, Md.). Activation-induced changes in interleukin-4 (IL-4), tumor necrosis factor (TNFα) interleukin-8 (IL-8):(R & D systems (Quantikine kit, Minneapolis, Minn.) and interferon-gamma (IFN-γ) (Endogen (Cambridge, Mass.) levels were determined using ELISA kits. All ELISA results were expressed as pg/ml and the CTLL-2 bioassay as counts per minute representing, the IL-2-dependent cellular incorporation of $^3$H-thymidine (ICN, Costa Mesa, Calif.) by CTLL-2 cells.

Figure 7:
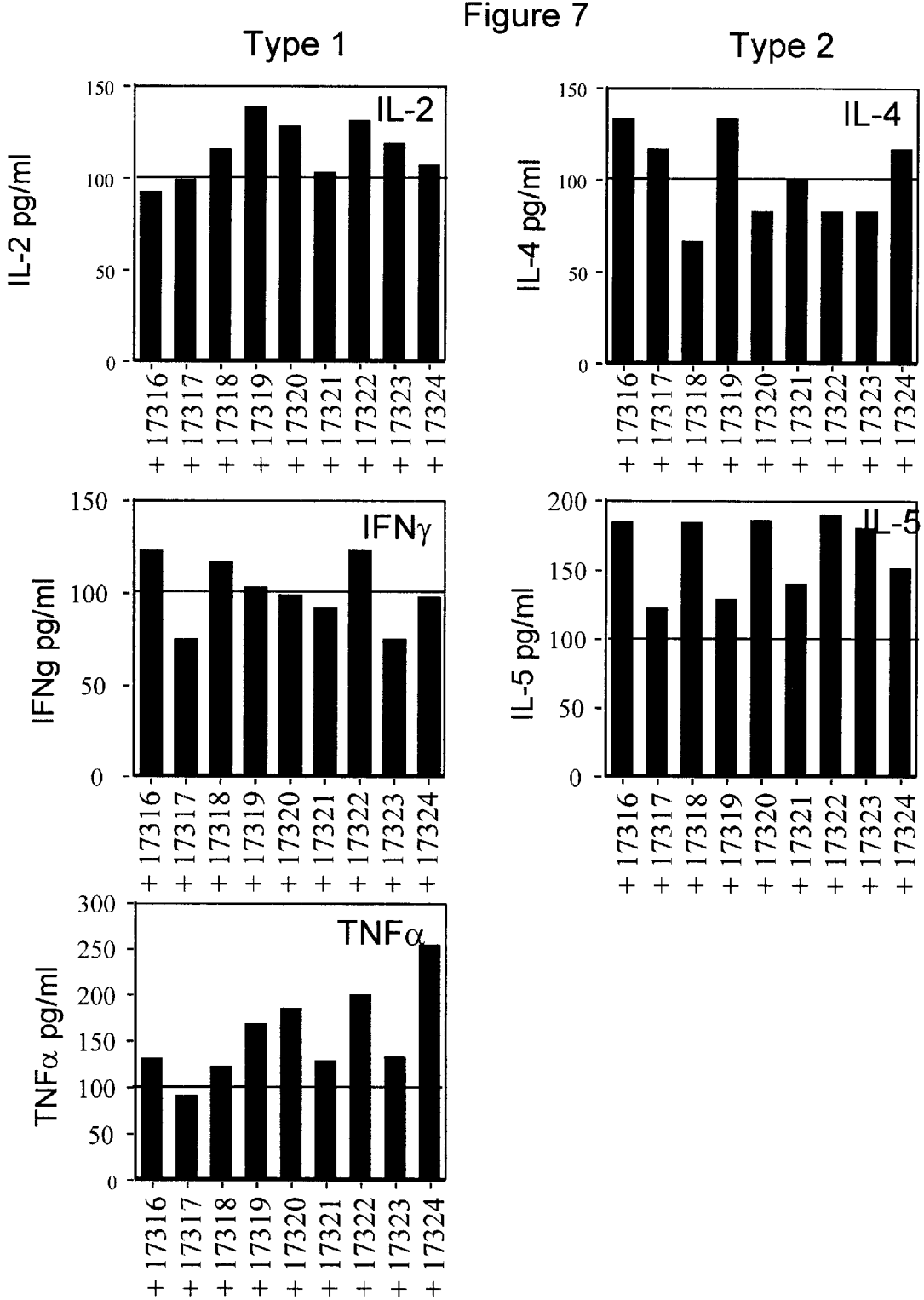
FIG. 7 is a graphical depiction of exemplary L-guanosine analogs on Th1 and Th2.

The results for each of the nine L-guanosine analogs on IL-2 TNFα, IFN-γ, IL-4 and IL-5 levels are presented in FIG. 7.

Synthesis

The compounds of the present invention may be produced according to synthetic methods which are individually readily known to those of ordinary skill in the art. In general, compounds according to the present invention are synthesized by condensing appropriate nucleoside base with the necessary sugar synthon to give the protected L-nucleoside which on further manipulation and deprotection of the sugar hydroxyl protecting groups will ultimately give rise to nucleoside analog having the desired ribofuranosyl moiety of the L-configuration.

Scheme 1 shows the synthesis of certain 7- and 8-substituted L-guanosine analogs. L-ribose 1 was methylated at C–1 and the resulting product 2 benzoylated to give compound 3, which was converted to 4 by treatment with acetic anhydride and in the presence of sulfuric acid. Reaction of 4 and silylated $N^2$-acetyl guanine in the presence of trimethylsilyl triflate gave compound 5 according to a commonly used procedure (Vorbrüggen et al. *Chem. Ber.*, 1981, 14, 1234). 5 was converted to 6 with ammonia in methanol. Bromination of 5 gave 8-bromo derivative 7, which was converted to 8-allyloxy-derivative 8 by treatment with allyl alcohol and sodium hydride. 8 was heated in water-methanol to yield 7-allyl-8-oxo derivative 9.

Scheme 2: 3-Deazaguanine 11 Cook et al. *J. Med. Chem.* 1976, 27, 1389) was treated with acetic anhydride in pyridine to yield $N^2$-acetyl-3-deazaguanine 12, which was silylated and coupled with 1-acetyl-2,3,5-O-tribenzoyl-L-ribose to give compound 13.

Scheme 3 shows the synthesis of 6-mercapto-L-guanosine and derivatives. $N^2$-Acetyl-2',3',5'-O-tribenzoyl-β-L- guanosine 5 was converted by treatment with phosphoruspentasulfide (Fox, et al. *J. Am. Chem. Soc.* 1958, 80, 1669) to 6-mercapto derivative 15, which was deprotected to give 6-mercapto-∃-L-guanosine 16. The sulfenamide derivative 17 was prepared by reaction of 16 with $NH_2$—Cl generated in situ. The sulfenamide 17 was oxidized with MCPBA to the sulfinamide 18 and sulfonamide 19 by controlling amount of the reagent (Revankar et al. *J. Med. Chem.* 1990, 33, 121).

Scheme 4 shows the synthesis of 1-β-L-ribofuranosylpyranzolo[3,4-d]pyrimidin-4(5H)-one and derivatives. The commercially available 4-hydroxypyranzolo[3,4-d]pyrimidine 20 was coupled with protected L-ribose to give the protected nucleoside 21, which was deprotected to give 1-β-L-ribofuranosylpyranzolo[3,4-d]pyrimidin-4(5H)-one 22. Similarly, 3-bromo-4-hydroxypyranzolo[3,4-d]pyrimidine 23 (Cottam et al. *J. Med. Chem.* 1984, 27, 1119) was coupled with L-ribose to give the protected nucleoside 24, which was deprotected to give 3-bromo-1-β-L-ribofuranosylpyranzolo[3,4-d]pyrimidin-4(5H)-one 25. Treatment of 24 with ammonia in the presence of copper and cuprous chloride at 100° C. yielded the 3-amino derivative 26.

Scheme 5 shows the synthesis of 8-aza-7-deaza-L-guanosine analogs. 3,6-Dibromopyrazolo[3,4-d]pyrimidin-4(5H)-one 27 (Petrie III et al. *J. Med. Chem.* 1985, 28, 1010) was coupled with protected L-ribose to give the nucleoside 28, which was treated with ammonia to give 8-aza-3-bromo-7-deaza-β-L-guanosine 29. Treatment of 28 with ammonia at 120° C. yielded 3-amino derivative 30. Hydrogenation of 29 over Pd/C gave 8-aza-7-deaza-β-L-guanosine 31 .

Scheme 6: 5-Aminothiazolo[4,5-d]pyriinidine-2,7(3H, 6H)-dione 32 (Baker et al. *J. Chem. Soc. C* 1970, 2478) was coupled with the deprotected ribose to give the nucleoside 33. Compound 33 can be protected with nitrophenethyl group and then treated with butyl nitrite and hydrogen fluoride in pyridine to give the fluoride derivative 35. Treatment of 33 with t-butyl nitrite (Nagahara et al. *J. Med. Chem.* 1990, 33, 407) in THF can replace the amino group with hydrogen to give 36.

The compounds described in the schemes 1–6 are β-L-guanosine analogs. The corresponding α-L-analogs can be prepared in a similar manner, but with L-rbose having different protecting groups. 1-Acetyl-2,3,5-O-tribenzoyl-L-ribofuranose can be replaced with 1-bromo-β-L-ribose derivatives as reagent, which would produce α-L-nucleosides as major products.

EXAMPLES

The following section give the experimental samples performed in the applicants' laboratory. The examples try to be broad, but not comprehensive. The work performed includes all the samples described below, but not limited to these examples.

Example 1

1-O-Methyl-L-ribofuranose 2

A cold solution of dry hydrogen chloride (4;4 g, 0.12 mmol) in methanol (100 mL) was slowly added to the solution of L-(+)-ribose 1 (50 g, 0.33 mole in methanol (1000 mL) at room temperature. After addition, the solution was stirred for 2.5 h and quenched with pyridine (100 mL). The mixture was stirred for 10 min and the solvent was evaporated. The residue was dissolved in pyridine (100 mL) and the resulting solution was concentrated to dryness to give 1-O-methyl-L-ribofuranose 2 as a pale-yellow syrup.

Example 2

1-O-Methyl-2',3',5'-O-tribenzoyl-L-ribofuranose 3

Benzoyl chloride (154.5 g, 1.1 mol) was added dropwise during 10 min to a solution of 1-O-methyl-L-ribofutanose 2 (0.33 mol) in pyridine (350 mL) at 0° C. After addition, the solution stood at room temperature for 14 h and quenched by stirring with water (500 mL) at 0° C. for 1 h. The aqueous layer was extracted with $CH_2Cl_2$ (2×100 mL) and the combined organic layer concentrated. The residue was dissolved in $CH_2Cl_2$ (500 mL), washed successively with saturated $NaHCO_3$ (3×100 mL), water (200 mL), brine (200 mL), dried over Na2SO4, filtered, and evaporated with toluene (2×300 mL). Further drying under vacuum afforded 1-O-methyl-2',3',5'-O-tribenzo-L-ribofuranose 3 as a yellow syrup (80 g, 0.17 mole).

Example 3

1-O-Acetyl-2',3',5'-O-tribenzoyl-L-ribofuranose 4

1-O-Methyl-2',3',5'-O-tribenzoyl-L-ribofuranose 3 (80 g, 0.17 mol) was dissolved at room temperature in a mixture of acetic acid (354 mL) and acetic anhydride (36 mL). The resulting solution was cooled to 0° C. and sulfuric acid (96%, 8.23 g, 0.084 mol) added. dropwise. After addition, the reaction mixture stood. at room temperature for 18 h, poured onto ice (500 g), and stirred until the ice had melt. EtOAc (1.2 L) was added followed by water (1 L). The organic layer was washed With water/brine mixture (4/1 ratio), saturated NaHCO3 (500 mL), brine (500 mL), filtered through a silica gel pad, and concentrated to give the crude product as yellow solid. Recrystallization from hexanes/EtOAc (300 mL/100 mL ratio) afforded 1-O-acetyl-2',3',5'-O-tribenzoyl-L-ribofuranose 4 as white needles (50 g, 59.6% overall yield from L-ribose).

Example 4

$N^2$-Acetyl-2',3',5'-O-tribenzoyl-β-L-guanosine 5

$N^2$-Acetylguanine (4.125 g, 21.35 mmol) was suspended in pyridine (50 mL) at 80° C. for 25 min. and then pyridine was evaporated under high vacuum. The same, procedure was repeated once. The obtained material was dried under vacuum overnight and silylated by heating with excess of HMDS (50 mL), pyridine (10 mL) and TMSCl (150 mL) under argon for 2.5 hours. After the reaction mixture was cooled to RT, the solvents were evaporated under vacuum. The residual HMDS and pyridine were coevaporated with xylene (2×40 mL). The silylated base was suspended in dichloroethane (70 mL) and combined with dichloroethane (182 mL) solution of 1-acetyl-2,3,5-O-tribezoyl-L-ribose (9.71 g, 19.22 mmol). The obtained suspension was stirred under argon at reflux temperature for 10 min. and dichloroethane (35 mL) solution of TMS-triflate (4.50 mL, 23.276 mmol) was added dropwise (20 min). The obtained reaction mixture was stirred under reflux for 1.5 h, cooled to RT and diluted with methylene chloride (500 ml). The organic solution was washed with cold NaHCO$_3$ (5% aq., 2×150 mL), brine (150 mL), dried. (Na$_2$SO$_4$) and evaporated to dryness. The reaction mixture was purified by flash chromatography (400 g of silica gel, eluent: 28% EtOAc, 2% EtOH in CH$_2$Cl$_2$, v/v) to give 5.60 g (46%) of N$^2$-Acetyl-2',3',5'-O-tribenzoyl-β-L-guanosine 5.

Example 6

8-Bromo-β-L-guanosine 7

To a suspension of L-guanosine 6 (1.24 g) in water (7.5 mL) was added in portions 35 mL of saturated bromine-water containing 0.35 mL of bromine. The solid was filtered off, successively washed with cold water, cold acetone, and dried. Crystallization from water gave pure 8-Bromo-L-guanosine 7 as a colorless solid.

Example 7

8-Allyloxy-β-L-guanosine 8

To a stirred mixture of NaH (984 mg) in anhydrous DMSO (30 mL) was added dropwise allyl alcohol (10 mL), followed by addition of 8-Bromo-L-guanosine 7 (1.78 g, 4.92 mmol) in DMSO (10 mL). The resulting reaction mixture was stirred at 60° C. overnight, cooled to room temperature, and diluted with ethyl ether (350 mL). The resulting precipitates were filtered, dissolved in water (18 mL), and neutralized with acetic acid. The resulting precipitates were filtered and recyrstallized from water/methanol to give 836 mg of 8-allyloxy-L-guanosine 8 as a slightly yellow solid.

Example 8

7-Allyl-8-oxo-β-L-guanosine 9

A mixture of 8-allyloxyguanosine 8 (560 mg) in methanol-water (50 mL, 1:1, v/v) was stirred under reflux and a clear solution formed after two hours. The solution was refluxed for additional 5 h and cooled to room temperature. A brown precipitates (by product) was filtered and the filtrate concentrated to give a crude product. Crystallization from water-ethanol gave 83 mg of title compound as a slightly brown solid. The filtrate was concentrated and the residue chromatographed on silica with 5%Et3N and 20% MeOH in methylene chloride to give 260 mg of 7-allyl-8-oxo-β-L-guanosine 9 as a colorless solid.

Example 10

N$^2$-Acetl-3-deazaguanine 12

To a suspension of 3-Deazaguanine 11 (2.0 g) in anhydrous pyridine (30 mL) was added acetic anhydride (5 mL) and the resulting reaction mixture heated to 90° C. Solid was dissolved gradually and a brown solution formed. After 10 minutes the precipitates reoccurred. The mixture was stirred at 90° C. for additional 90 minutes and cooled to 50° C. The precipitates were filtered and washed with acetonitrile, water, and acetonitrile again to give 1.79 g of N$^2$-acetyl-3-deazaguanine 12 as a light-brownsolid.

Example 11

N$^2$-Acetyl-3-deaza-β-L-guanosine 14

A suspension of N$^2$-acetyl-3-deazaguanine 12 (576 mg, 3.0 mmol), hexamethyldisilazane (HMDS, 15 mL), pyridine (2 mL), and ammonium sulfate (10 mg) was stirred under reflux and exclusion of moisture for 2.5 h. Solvents were evaporated and the residue dried under vacuum for 2 h to give a foam syrup. The residue was dissolved in methylene chloride (anhydrous, 30 L) and 1-Acetyl-2,3,5-tribenzoyl-L-robose (1.51 g, 3.0 mmol) added, followed by slow addition of trimethylsilyl triflate (4.5 mmol, 0.81 mL). The resulting solution was refluxed for 20 h. Solvent was evaporated and the residue dissolved in ethyl acetate, washed with 5% NaHCO3, dried (NA2SO$_4$), and concentrated. Chromatography on silica with 5% Et3N and 2–10% ethanol in methylene chloride gave three major products: 340 mg of higher Rf product, 368 mg of the medium Rf product 13, and 335 mg of the lower Rf product, all as a slightly yellow solid.

Example 12

N$^2$-Acetyl-6-mercapto-2',3',5'-O-tribenzoyl-β-L-guanosine 15

To a stirred suspension of N$^2$-acetyl-2',3',5'-O-tribenzoyl-L-guanosine 5 (5.60 g, 8.78 mmol) and phosphoruspentasulfide (8.0 g, 36.0 mmol) in pyridine (210 mL) was added dropwise water (590 mL) and the resulting reaction mixture heated at reflux temperature for 8 h. A few drops of water was added whenever the solution began to lose its turbidity. At the end of reflux period pyridine was evaporated to give a thin syrup, which was added slowly to vigorously stirred, boiling water (1000 mL). The resulting mixture was stirred for 45 minutes and extracted with EtOAc (3×250 mL). The organic layer was washed with brine (2×200 mL), water (2×100 mL), dried (Na$_2$SO$_4$), and evaporated to dryness. Chromatography on silica gel (400 g) with 23% EtOAc, 2% EtOH in CH$_2$Cl$_2$ (v/v) to give 3.53 g (61.5%) of N$^2$-acetyl-6-mercapto-2',3',5'-O-tribenzoyl-β-L-guanosine 15 as a colorless solid.

Example 13

6-Mercapto-β-L-guanosine 16

A solution of N$^2$-acetyl-6-mercapto-2',3',5'-O-tribenzoyl-L-guanosine 15 (3.53 g, 5.40 mmol) in saturated ammonia-methanol (200 mL) was stirred at room temperature for 62 hours. Ammonia and methanol were evaporated and the residue was triturated with chloroform. The precipitates were filtered and washed with warm chloroform (50 mL), redissolved in dilute aqueous ammonia, and acidified with acetic acid. The resulting precipitates were filtered and dried under vacuum to give 1.48 g.(91.6%) of 6-mercapto-β-L-guanosine 16 as a colorless solid.

Example 14

2-Amino9-(β-L-ribofuranosyl)purine-6-sulfenamide 17

To a stirred aqueous sodium hypochlorite solution (5.25%, 2.25 mL, 1.725 mmol) cooled to 0° C. in an ice bath was added ammonium hydroxide (1.4 M, 6 mL, 8.4 mmol) cooled to 0° C. The resulting mixture was stirred at 0° C. for 15 minutes and a cold (0° C.) solution of 6-mercapto-L-guanosine 16 (450 mg, 1.5 mmol) in 2M KOH (750 mL) was added. The reaction mixture was stirred for 2 h until it had warmed to room temperature. The resulting precipitates were filtered off, washed with cold EtOH, filtered, and dried to give 240 mg (51%) of 2-amino-9-(β-L-ribofuranosyl)purine-6-sulfenamide 17 as a colorless solid.

Example 15

2-Amino-9-(β-L-ribofuranosyl)purine-6-sulfinamide 18

A mixture of 2-amino-9-(β-L-ribofiiranosyl)purine-6-sulfenamide 17 (200 mg, 0.637 mmol), ethanol (90 mL) and water (6.4 mL) was vigorously stirred at −10° C. in a salt-ice bath. A solution of MCPBA (80%, 137.0 mg, 0.637 mmol) in ethanol 5.5 mL was added dropwise over a period of 15 minutes. The mixture was allowed to stir and warm as the ice melt (8 h), and stirred at ambient temperature for addition 14 h. A small amount of precipitate was filtered out and the filtrate evaporated at 23° C. to dryness. The residue was triturated with ethyl ether (30 mL) and the solid was collected by filtration, washed with ethyl ether (10 mL). The solid was again suspended in ethyl ether (25 mL), filtered, and dried to give 182 mg (87%) of 2-amino-9-(β-L-ribofuranosyl)purine-6-sulfinamide 18 as a colorless solid.

Example 16

2-Amino-9-(β-L-ribofuranosyl)purine-6-sulfonamide 19

To a stirred suspension of 2-amino-9-(β-L-ribofuranosyl)purine-6-sulfenamide 17 (150 mg, 0.478 mmol) in ethanol (28.5 mL) and water. (2.8 mL) at room temperature was added in portions during 1 hour a solution of MCPBA (80%, 412.0 mg, 1.91 mmol) in ethanol (2.8 mL). The reaction mixture became clear after 3 h. The solution was stirred for an additional 15 h at ambient temperature and became cloudy. The reaction mixture was concentrated at room temperature to dryness. The residue was triturated with ethyl ether (30 mL) and the solid was collected by filtration. The crude product was dissolved in methanol/water mixture and adsorbed onto silica gel (2.0 g). Solvent was evaporated and the dry silica bearing the product was loaded onto a flash silica column (100 g) packed in methylene chloride. The column was eluted with 20% MeOH in $CH_2Cl_2$ (v/v)to give 87 mg (52.6%) of 2-Amino-9-(β-L-ribofuranosyl)purine-6-sulfonamide 19 as a colorless solid.

Example 17

1-(2',3',5'-O-Tribenzoyl-β-L-ribofuranosyl)pyrazolo [3,4-d]pyrimidin-4(5H)-one 21

A mixture of 4-Hydroxypyrazolo[3,4-d]pyrimidine 20 (100 mg, 0.74 mmole), 1,1,1,3,3,3-hexamethyidisilazane (HMDS, 10 mL), and $(NH_4)_2SO_4$ (10 mg, 0.076 mmole) was heated under reflux for 3 h to form a clear solution. The excess HMDS was evaporated to give a yellow solid, which was dried under vacuum for 15 min. 1-O-Acetyl-2',3',5'-O-tribenzoyl-L-ribofuranose (370 mg, 0.74 mmol) was added, followed by addition of acetonitrile (anhydrous, 5 mL). Trimethylsilyl trifluoromethanesulfonate (245 mg, 1.1 mmol) was added dropwise to the above slurry at room temperature. After addition, the clear solution stood at room temperature for 14 h. Solvent was evaporated and the yellow residue dissolved in EtOAc (50 mL), washed with saturate $NaHCO_3$ (2×20 mL), water (3×20 mL), dried over $Na_2SO_4$, and concentrated. Flash chromatography on silica (5% methanol in methylene chloride) gave 1-(2',3',5'-O-tribenzoyl-β-L-ribofuranosyl)pyrazolo[3,4-d]pyrimidin-4 (5H)-one 21 as a white solid (177 mg, 41.5%).

Example 18

1-β-L-Ribofuranosylpyrazolo[3,4-d]pyrimidin-4 (5H)-one 22

1-(2',3',5'-O-Tribenzoyl-β-L-ribofuranosyl)pyrazolo[3,4-d]pyrimidin-4(5H)-one 21 (152 mg, 0.26 mmole) was dissolved in MeOH saturated with $NH_3$ at 0 C (75 mL). The resulting solution stood at room temperature for 24 h and concentrated. The residue was dissolved in water (30 mL), washed with EtOAc (3×15 mL). After evaporation of the water, the crystalline solid was soaked in acetonitrile (2 mL), filtered, and dried under vacuum to give 1-β-L-ribofuranosylpyrazolo[3,4-d]pyrimidin-4(5H)-one 22 as a white crystalline solid (70 mg, 99%).

Example 19

3-Bromo-1-(2',3',5'-O-tribenzoyl-β-L-ribofuranosyl) pyrazolo[3,4-d]pyrimidin-4(5H)-one 24

Acetonitrile (30 mL) was added to a mixture of 3-bromnopyrazolo[3,4-d]pyrimidin-4(5H)-one 23 (1.08 g, 4.0 mmoles) ard 1-O-acetyl-2',3',5'-O-tribenzoyl-β-L-ribofuranose (3.02 g, 6.0 mmoles). The resulting slurry was heated to reflux and trifluoroborane etherate (851 mg, 6.0 mmoles) added dropwise. The resulting solution was heated under reflux overnight. Solvent was evaporated, residue dissolved in EtOAc (100 mL), the resulting solution washed with saturated $NaHCO_3$, water, dried over $Na_2SO_4$, ad concentrated. Flash chromatography on silica (5% acetone in methylene chloride) afforded 3-Bromo-1-(2',3',5'-O-tribenzoyl-β-L-ribofuranosyl)pyrazolo[3,4-d]pyrimidin-4 (5H)-one 24 as a pale-yellow solid (1.1 g, 41.7%).

Example 20

3-Bromo-1-β-L-ribofuranosylpyrazolo[3,4-d] pyrimidin-4(5H)-one 25

3-Bromo-1-(2',3',5'-O-tribenzoy-β-L-ribofuranosyl)pyrazolo[3,4-d]pyrimidin-4(5H)-one 24 (280 mg, 0.43 mmole) was dissolved in MeOH saturated with $NH_3$ at 0 C (25 mL). The solution in a sealed, stainless steel bomb was heated at 100 C for 6 h. After cooling, ammonia and methanol were evaporated. The residue was dissolved in water (40 mL), washed with EtOAc (4×20 mL), and concentrated. The residue was soaked in acetonitrile and the resulting solid filtered, dried under vacuum to give 3-Bromo-1-β-L-ribofuranosylpyrazolo[3,4-d]pyrimidin-4 (5H)-one 25 as a white solid (140 mg, 95%).

Example 21

3-Amino-1-β-L-ribofuranosylpyrazolo[3,4-d] pyrimidin-4(5H)-one 26

3-Bromo-1-(2',3',5'-O-tribenzoyl-β-L-ribofdranosyl)pyrazolo[3,4-d]pyrimidin-4(5H)-one 24 (714 mg, 1.08 mmoles) was dissolved in MeOH saturated with NH$_3$ at 0 C (30 mL). Thin copper wire (21 mg, 0.33 mmole) and cuprous chloride.(33 mg, 0.33 mmole) were added. The mixture in a sealed, stainless steel bomb was heated at 100 C for 16 h. After cooling, silica gel (2 g) was added to the reaction mixture and, the solvent evaporated. The silica gel absorbed with the crude product was loaded onto a silica column and eluted with 5% Et$_3$N, 17% MeOH in CH$_2$Cl$_2$). The product was further purified by recrystallization (95% EtOH) to afford 3-amino-1-β-L-ribofuranosylpyrazolo[3,4-d] pyrirnidin-4(5H)-one 26 as a white needles (110 mg, 36%).

Example 22

3,6-Dibromo-1-(2',3',5'-O-tribenzoyl-β-L-ribofuranosyl)pyrazolo[3,4-d]pyrimidin-4(5H)-one 28

Acetonitrile (80 mL) was added to, a mixture of 3,6-Dibromopyrazolo[3,4-d]pyrimidin-4(5H)-one 27 (1.18 g, 4.0 mmol) and 1-O-acetyl-2',3',5'-O-tribenzoyl-ribofuranose (3.02 g, 6.0 mmol). The slurry was heated to reflux, followed by slow addition of trifluoroborane etherate (851 mg, 6.0 mmol). The reaction mixture was heated under reflux for 6 h. After removal of solvent, the residue was dissolved in EtOAc (200 mL), washed with saturated NaHCO$_3$ (2×50 mL), water (2×50 mL), dried (Na$_2$SO$_4$), and concentrated. The crude product was purified by flash chrormatography on silica (5% acetone in methylene chloride) to give (1.49 g, 50.5%) of 3,6-Dibromo-1-(2',3',5'-O-tribenzoyl-β-L-ribofuranosyl)pyrazolo[3,4-d]pyrimidin-4(5H)-one 28 as a yellow foam.

Example 23

3-Bromo-7-deaza-8-aza-β-L-guanosine 24

3,6-Dibromo-1-(2',3',5'-O-tribenzoyl-β-L-ribofuranosyl) pyrazolo[3,4-d]pyrimidin-4(5H)-one (260 mg, 0.35 mmole) 28 was dissolved in MeOH saturated with NH$_3$ at 0 C (20 mL). The solution in a sealed, stainless steel bomb was heated at 120 C for 16 h. After cooling and removal of solvent, the residue was dissolved in water (100 mL), washed with CH$_2$Cl$_2$ (5×15 mL), and concentrated to give a yellow solid. The solid was dissolved in a mixture of methanol and methylene chloride (1:1) and passed through a silica gel pad. The filtrate was concentrated and the solid residue dissolved in MeOH (5 mL), followed by slow addition of diethyl ether (40 mL). The resulting precipitates were filtered, washed with diethyl ether (2×2 mL), and dried under vacuum to give 3-bromno-7-deaza-8-aza-β-L-guanosine 29 as an off-white solid (102.2 mg, 80.2%).

Example 24

3-Amino-7-deaza-8-aza-L-guanosine 25

3,6-Dibromo-1-(2',3',5'-O-tribenzoyl-β-L-tribofuranosyl) pyrazolo[3,4-d]pyrimidin-4(5H)-one 28 (500 mg, 0.68 mmole) was dissolved in MeOH saturated with NH$_3$ at 1 C (50 mL), followed by addition of thin copper wire (21.5 mg, 0.34 mmole) and cuprous chloride (19.8 mg, 0.20 mmole). The mixture in a sealed, stainless steel bomb was heated at 120 C for 16 h. After cooling and removal of solvent, the residue was dissolved in MeOH, the solid filtered, and the filtrate concentrated. Purification of the residue by flash chromatography on silica (20% MeOH in CH$_2$Cl$_2$) gave 3-amino-7-deaza-8-aza-L-guanosine 30 as a white solid (62 mg, 30.9%).

Example 25

7-Deaza-8-aza-L-guanosine 26

3-Bromo-7-deaza-8-aza-β-L-guanosine 29 (246 mg, 0.68 mmole) was dissolved in EtOH (50%, 60 mL), followed by addition of 10% Pd/C (67 mg). The mixture was shaken at 50 psi hydrogen at room temperature for 6 h. The Palladium catalyst was filtered and the filtrate concentrated. The crude product was dissolved in MeOH, followed by addition of silica gel (2 g). After removal of methanol, the dry silica gel adsorbed with the crude product was loaded onto a silica column and eluted with 17% MeOH in CH2Cl2) to give 7-Deaza-8-aza-β-L-guanosine 31 as a white solid (102.4 mg, 53.2%).

Example 26

5-Amino-3-(2',3',5'-O-tribenzoyl-β-L-ribofuranosyl) thiazolo[4,5-d]pyrimidine-2,7(6H)-dione 34

5-Aminothiazolo[4,5-d]pyrimidine-2,7(6H)-dione 32 (400 mg, 2.71 mmol) was suspended in acetonitrile (16 mL) and hexamethyldisilazane (0.96 mL), and trimethylchlorosilane (0.55 mL) and trimethylsilyl triflate (0.9 mL) added. The mixture was stirred under reflux for 3.5 h. A solution of trimethylsilyl triflate (0.45 mL) in acetonitrile (1.0 mL) was added dropwise and stirring and heating was continued for additional 30 min. A slurry of 1-O-acetyl-2,3,5-O-tribenzoyl-L-ribofuranose (1.22 g, 2.28 mmol) in acetonitrile (4.1 mL) was added and the mixture stirred under reflux for 30 min. The reaction mixture was cooled and slowly poured into a vigorously stirred mixture of sodium bicarbonate (2.81 g) and water (96 mL), which produced a stick solid. Ethyl acetate was added, the mixture stirred until the solid dissolved. The aqueous layer was extracted with ethyl acetate twice and the combined organic layer washed with sodium bicarbonate, dried (Na2SO4), and concentrated. The crude was purified by chromatography on silica with 5% Et3N and 5% ethanol in methylene chloride to give 1.10 g of 5-amino-3-(2',3',5'-O-tribenzoyl-β-L-ribofuranosyl) thiazolo[4,5-d]pyrimidine-2,7(6H)-dione 33 as a white solid.

Example 28

Methyl 5-cyanomethyl-1-(2,3,5-O-tribenzoyl-L-ribofuranosyl)imidazole-4-carboxylate.

Methyl 5-cyanomethylimidazole-4-carboxylate (Robins et al. *J. Org. Chem.* 1963, 28, 3041, 500 mg, 3.02 mmol) was refluxed under anhydrous conditions for 12 h with HMDS (8 mL) and ammonium sulfate (30 mg). The excess HMDS was removed by distillation under reduced pressure to give the

21 trimethylsilyl derivative as a yellowish brown oil. The oil was dissolved in dry 1,2-dichloroethane (20 mL) and 1-O-acetyl-2,3,5-O-tribenzoylribofuranose (1.53 g, 3.03 mmol) was added, followed by addition of stannic chloride (516 mL, 4.39 mmol). The reaction mixture Was stirred at ambient temperature for 18 h and then poured into a cold 5% NaHCO₃ aqueous solution (50 mL). The precipitates were filtered through Celite and the filtrate extracted with chloroform (3×50 mL). The extracts were dried (Na₂SO₄) and evaporated under reduced pressure to give a light-beige foam (1.8 g). This material was purified by chromatography on silica with hexanes-ethylacetate (1:1) to yield 1.65 g (89%) of Methyl 5-cyanomethyl-1-(2,3,5-O-tribenzoyl-L-ribofuranosyl)imidazole-4-carboxylate as a colorless solid.

Example 29

3-Deaza-β-L-guanosine

Methyl 5-cyanomethyl-1-(2,3,5-O-tribenzoyl-L-ribofuranosyl)imidazole-4-carboxylate (1.03 g, 1.69 mmol) was dissolved in methanol (60 mL) and saturated with anhydrous ammonia at 0° C. The reaction mixture was placed in a sealed steel bomb and kept at 100° C. for 18 h. The mixture was cooled to r.t. and evaporated to dryness. The residue was suspended in warm chloroform, and remaining solid was filtered, washed with chloroform (5×10 ml), and dried. The crude product was recyrstallized from water to yield 320 mg (70%) of 3-Deaza-(3-L-guanosine as a colorless solid.

Example 30

3-Bromo-3-deaza-β-L-guanosine 40

To a stirred solution of 3-deaza-β-L-guanosine (200 mg, 0.708 mmol) in 8 mL of water/methanol (1:1) at 0° C. was added bromine (20 mL, 0.39 mmol) was added. After stirring for 15 min. the reaction mixture was evaporated to dryness. The crude material was suspended in chloroform, filtered, and dried to yield 210 mg (82%) of 3-bromo-3-deaza-β-L-guanosine as a colorless solid.

We claim:

1. A compound consisting of either an 8-substituted α-L-guanosine analog according to Formula 1-A or an 8-substituted β-L-guanosine analog according to Formula 1-A':

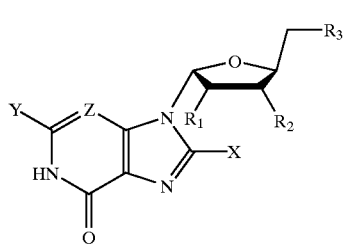

Formula 1-A

22

-continued

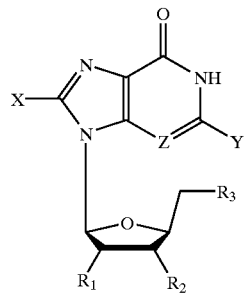

Formula 1-A' wherein X is selected from the group consisting of H, R, F, Cl, Br, I, N₃, —CN, —OR, —SR, —NR₂, —NHNH₂, —NHOH, —CHO, —CONH₂, —COOR, and -L-A; where R is selected from the group consisting of alkyl, alkenyl, alkynyl, and aralkyl, acetyl, acyl, and sulfonyl; L is a linker and selected from alkyl, alkenyl, alkynyl, and aralkyl; and A is selected from the group consisting of H, —OR', —SR', —NR'₂, —NHNH'₂, —CHO, —COOR', and —CONR'₂, where R' is selected from the group consisting of H, Me, Et, allyl, acetyl, and —COCF₃;

Y is selected from the group consisting of H, R, F, Cl, Br, I, N₃, CN, OR, SR, and NR₂, where R is selected from the group consisting of H, alkyl, alkenyl, alkynyl, and aralkyl, acetyl, acyl, and sulfonyl;

Z is N or CH; and

R₁, R₂, and R₃ are independently selected from H, —OH, —OAc, —OBz, and —OP(O₂)OH;
  with the provisos that when X is a halogen, H, OH, SH or NH₂, and/or Y is a halogen, H, OH, SH or NH₂, then R₂ and/or R₃ cannot be H;
  when R₁ and R₂ are OH, X and Y are not H; and
  when R₁ and R₂ are H, X and Y are not H, and Y is not NH₂.

2. A compound consisting of either a 7-substituted-8-oxo-α-L-guanosine analog according to Formula 1-B or a 7-substituted-8-oxo-β-L-guanosine analog according to Formula 1-B':

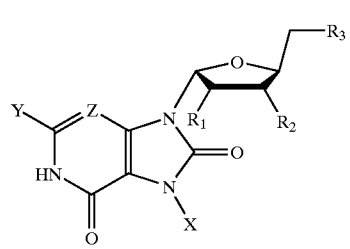

Formula 1-B

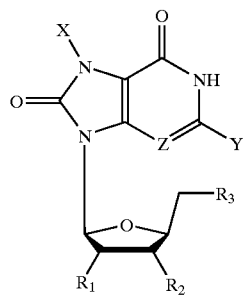

Formula 1-B' wherein X is selected from the group consisting of H, R, —NH$_2$, —CHO, —COOR, and -L-A, where R is selected from the group consisting of alkyl, alkenyl, alkynyl, and aralkyl; L is a linker and selected from alkyl, alkenyl, alkynyl, and aralkyl; A is selected from the group consisting of H, F, Cl, Br, I, —OR', —SR', —NR'$_2$, —NHNH$_2$, —NHOH, N$_3$, —CHO, —CONH$_2$, —COOR', and —, where R' is selected from the group consisting of Me, Et, allyl, acetyl, and —COCF$_3$;

Y is selected from the group consisting of H, R, F, Cl, Br, I, N$_3$, —CN, —OR, —SR, and —NR$_2$, where R is selected from the group consisting of H, alkyl, alkenyl, alkynyl, and aralkyl, acetyl, acyl, and sulfonyl;

Z is N or CH; and

R$_1$, R$_2$, and R$_3$ are independently selected from the group consisting of H, —OH, —OAc, —OBz, and —OP(O$_2$)OH;

with the proviso that where R$_1$, R$_2$, and R$_3$ are OH, then Z is not N, Y is not NH$_2$, and X is not propyl.

3. A compound consisting of either a 7-deaza-8-aza-7-α-L-guanosine analog according to Formula 1-D or a 7-deaza-8-aza-7-β-L-guanosine analog according to Formula 1-D':

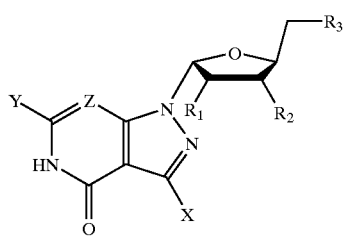

Formula 1-D

Formula 1-D'

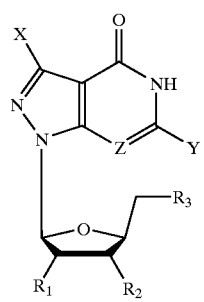

wherein X is selected from the group consisting of H, R, F, Cl, Br, I, N$_3$, —CN, —OR, —SR, —NR$_2$, —NHNH$_2$, —NHOH, —CHO, —CONH$_2$, —COOR, and -L-A; where R is selected from the group consisting of alkyl, alkenyl, alkynyl, and aralkyl, acetyl, acyl, and sulfonyl; L is a linker and selected from the group consisting of alkyl, alkenyl, alkynyl, and aralkyl; and A: is selected from the group consisting of H, —OR', SR', —NR'$_2$, —NHNH$_2$, —CHO, —COOR', —CONR'$_2$, where R' is selected from the group consisting of H, Me, Et, allyl, acetyl, and —COCF$_3$;

Y is selected from the group consisting of H, R, F, Cl, Br, I, N$_3$, —CN, —OR, —SR, and —NR$_2$, where R is selected from the group consisting of H, alkyl, alkenyl, alkynyl, aralkyl, acetyl, acyl, and sulfonyl;

Z is N or CH; and

R$_1$, R$_2$, and R$_3$ are independently selected from the group consisting of H, —OH, —OAc, —OBz, and —OP(O$_2$)OH.

4. A compound consisting of either a thiazolopyrimidine α-L-nucleoside according to Formula 1-E or a thiazolopyrimidine β-L-nucleoside according to Formula 1-E':

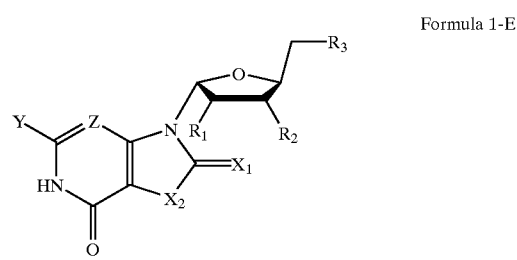

Formula 1-E

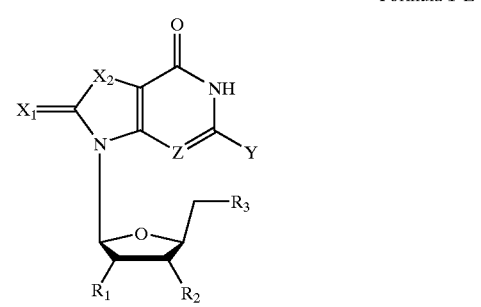

Formula 1-E' wherein X$_1$ is selected from the group consisting of O, S, =NH, =NNH$_2$, =NHOH, =NR where R is selected from the group consisting of alkyl, alkyenyl, alkynyl, aralkyl, and acyl;

X$_2$ is S, O, or Se;

Y is selected from the group consisting of H, R, F, Cl, Br, I, N$_3$, —CN, —OR, —SR, and —NR$_2$, where R is selected from H, alkyl, alkenyl, alkynyl, aralkyl, acetyl, acyl, and sulfonyl;

Z is N or CH; and

R$_1$, R$_2$, and R$_3$ are independently selected from the group consisting of H, —OH, —OAc, —OBz, and —OP(O$_2$)OH.

5. A pharmaceutical composition comprising a compound according to any one of claims 2 or 3, or a pharmaceutically acceptable ester or salt thereof, admixed with at least one pharmaceutically acceptable carrier.

* * * * *